United States Patent [19]
Ganci

[11] Patent Number: 5,847,143
[45] Date of Patent: Dec. 8, 1998

[54] PROCESS FOR PREPARING QUINACRIDONES

[75] Inventor: James B. Ganci, Wilmington, Del.

[73] Assignee: Ciba Specialty Chemicals Corporation, Tarrytown, N.Y.

[21] Appl. No.: 715,058

[22] Filed: Sep. 17, 1996

Related U.S. Application Data

[60] Provisional application No. 60/004,189 Sep. 22, 1995.

[51] Int. Cl.⁶ .................................................. C09B 48/00
[52] U.S. Cl. .............................................. 546/56; 546/49
[58] Field of Search ........................................ 546/49, 56

[56] References Cited

U.S. PATENT DOCUMENTS

| | | | |
|---|---|---|---|
| 2,821,529 | 1/1958 | Struve | 546/49 |
| 2,982,666 | 5/1961 | Chun et al. | 546/56 |
| 3,024,239 | 3/1962 | Caliezi | 546/49 |
| 3,475,436 | 10/1969 | Cooper et al. | 546/49 |
| 3,738,988 | 6/1973 | Jackson | 546/49 |
| 5,093,497 | 3/1992 | Schütz et al. | 546/56 |
| 5,229,515 | 7/1993 | Pfenninger et al. | 546/49 |
| 5,286,863 | 2/1994 | Bäbler et al. | 546/56 |
| 5,424,429 | 6/1995 | Hendi | 546/56 |
| 5,457,203 | 10/1995 | Hendi | 546/56 |
| 5,502,192 | 3/1996 | Ganci | 546/49 |
| 5,610,306 | 3/1997 | Maki et al. | 546/56 |
| 5,659,036 | 8/1997 | Maki | 546/49 |

*Primary Examiner*—Donald G. Daus
*Attorney, Agent, or Firm*—Kevin T. Mansfield; George R. Dohmann

[57] ABSTRACT

This application relates to a process for preparing quinacridones whereby the corresponding dihydroquinacridone is oxidized by subjecting a paste containing the dihydroquinacridone and an oxidizing agent to a high shear force mixing step.

21 Claims, No Drawings

PROCESS FOR PREPARING QUINACRIDONES

This application claims the benefit under 35 U.S.C. 119(e) of U.S. Provisional application Ser. No. 60/004,189, filed Sep. 22, 1995.

SUMMARY

Disclosed is a process for oxidizing a dihydroquinacridone to a quinacridone by subjecting a paste containing the dihydroquinacridone to a high shear force mixing step.

BACKGROUND

Quinacridone pigments are well known in the art and can be prepared by a number of processes some of which involve oxidizing an unsubstituted or substituted 6,13-dihydroquinacridone to the correspondingly substituted quinacridone.

Numerous publications disclose processes wherein the dihydroquinacridone is oxidized to the quinacridone in a solution or suspension, for example a DMSO solution or an aqueous, alcoholic or organic liquid suspension.

For example, U.S. Pat. No. 2,821,529 describes a process wherein various 6,13-dihydroquinacridones (DQA) are oxidized to the corresponding quinacridone (QA) by heating a suspension containing the dihydroquinacridone and a mild oxidizing agent in an alkaline reaction medium. The medium is a mixture containing a major portion of an organic liquid, generally an alcohol, and a minor amount of water. The amount of water present in the reaction medium is small relative to the amount of the organic liquid.

The literature also describes processes for oxidizing a dihydroquinacridone to the corresponding quinacridone by utilizing molecular oxygen and a quinone compound as the oxidizing agent. Such a reaction is often referred to as an "air oxidation" because air is a preferred source of the molecular oxygen. In general, such oxidation processes are disclosed as taking place in an alkaline medium, usually an organic liquid containing a minor amount of water, in the presence of a quinone compound and molecular oxygen. The molecular oxygen is introduced to the reaction medium by bubbling an oxygen containing gas through the reaction medium or by blowing the oxygen containing gas above the surface thereof. Although the literature describes the quinone compound both as a catalyst and as an oxidizing agent, U.S. Pat. No. 3,024,239 discloses that the quinone is an oxidizing agent which is reduced to the corresponding leuco compound during the oxidation of the dihydroquinacridone. The molecular oxygen regenerates the quinone so that less than the stoichiometric amount of the quinone is required for the reaction to proceed to completion.

U.S. Pat. No. 3,475,436 discloses an air oxidation process wherein the reaction medium is a suspension which contains a major portion of tetramethylene sulfone and a relatively small amount of water. Similar processes which utilize an alkaline medium containing a major portion of other organic liquids, such as dimethylacetamide, alkanediols, $C_1$–$C_3$ alcohols caprolactam and N-alkyl-2-pyrrolidone, usually in the presence of a relatively small amount of water, are also known in the art.

It is also known that air oxidation proceeds when the reaction medium is a solution containing a salt of the DQA in solution. For example, U.S. Pat. No. 5,286,863 discloses a process wherein the reaction medium is a basic DMSO solution of the DQA which additionally contains a base and a quinone catalyst.

It is also known to perform the air oxidation of dihydroquinacridones in an aqueous reaction medium. For example, U.S. Pat. No. 3,738,988 discloses a process wherein an aqueous medium is utilized in the presence of divalent iron, cobalt or nickel ions in order to increase the effectiveness of the oxidation. U.S. Pat. No. 5,093,497 requires the presence of a quaternary ammonium salt in order to overcome disadvantages in known air oxidation processes in both an aqueous reaction medium or an organic reaction medium.

In each instance, the oxidation is accomplished in a highly basic suspension or solution of the QA and oxidizing agent at temperatures ranging from about 70° to 125° C.

The present invention is based on the discovery that excellent conversion of the 6,13-dihydroquinacridone to the corresponding quinacridone is achieved by subjecting a viscous paste comprising a 6,13-dihydroquinacridone, an oxidizing agent and a base to a high shear force mixing step. Advantageously, the paste also contains a small amount of an organic conditioning agent, such as polyethylene glycol, and/or a substantial amount of a grinding aid, such as sodium chloride. Such an approach permits oxidation and finishing to progress simultaneously to yield a pigmentary quality quinacridone directly from the oxidation step. Omission of the organic conditioning agent or the use of a non-volatile organic conditioning agent permits the process to be carried out in a vessel which is open to the atmosphere. Additional advantages are realized when the oxidizing agent is a quinone which can be used in less than the stoichiometric amount because ambient air (oxygen) regenerates the catalyst, thereby reducing organic waste products.

DETAILED DESCRIPTION

The present invention relates to a process for preparing a unsubstituted or substituted quinacridone from a correspondingly substituted dihydroquinacridone, which comprises subjecting a paste containing the dihydroquinacridone and an oxidizing agent to a high shear force mixing step.

In this application, the expression "paste" refers to the physical form of the mixture containing the DQA and oxidizing agent and is intended to have its common meaning. In particular, "paste" is intended to mean a solid or semisolid physical form which is viscous, pliable and capable of being deformed continuously in any direction. For example, the paste used in the present process normally has a consistency which requires mixers of the heavy duty type, such as the BAKER-PERKINS dispersion mixer or the BANBURY mixer. While oxidation may be carried out at lower paste viscosity, if desired, simultaneous particle size reduction of the oxidized product is best effected at higher paste viscosity.

Preferably, the paste utilized as the reaction medium for the present oxidation step is similar or identical in physical form to the paste that is formed during known pigment conditioning processes used to convert crude pigment forms to a pigmentary form. For example, U.S. Pat. No. 2,982,666, discloses subjecting a viscous paste containing a pigment crude, a grinding aid and an organic conditioning agent to a high shear force mixing step in a heavy duty masticator.

In general, the high shear force mixing step is carried out in any apparatus that is capable of providing sufficient mixing of the paste to effect oxidation of the DQA. The kneader is a particularly suitable apparatus for carrying out the high shear force mixing step; for example, a one quart capacity BAKER-PERKINS model ML-14. Generally, the mixing is continued until the oxidation of DQA to QA is complete. Under normal circumstances, the mixing is continued for a period of from 1 to 6 hours, preferably for from 1 to 3 hours. Although the oxidation is usually complete within about three hours, if a pigmentary product is desired, it may be advantageous to extend the mixing time to reduce the particle size of the product.

In general, the expression "high shear force" is defined in terms of the shaft horsepower of the kneader. For example, with a 150 gram batch of paste, a kneader with ⅙ horsepower provides adequate shear force.

The paste comprises at least the DQA and the oxidizing agent However, the presence of a base is required in order for the reaction to proceed at a reasonable rate. In addition, the presence of some liquid is required in order to have a pasty physical form. It is also advantageous to include an organic conditioning agent and/or a substantial amount of a grinding aid in the paste. The grinding aid is required if a product with pigmentary properties is desired Unsubstituted and substituted 6,13-dihydroquinacridone compounds are well-known in the art and can be prepared, for example, from 2,5-diarylamino-3,6-dihydroterephthalic esters by processes known in the art Any DQA that can be oxidized to a quinacridone is suitable for use in the present process. Dihydroquinacridone compounds that are especially suitable to be oxidized by the present process include those of the formula

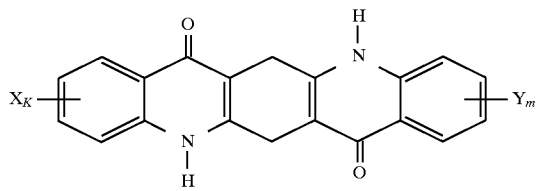

wherein X and Y are independently H, halogen, in particular F or Cl, carboxyl, $C_1$–$C_4$alkyl, $C_1$–$C_4$alkyl that is substituted by halogen, for example trifluoromethyl, or $C_1$–$C_4$alkoxy and k and m are integers from 0 to 2. Any substituted DQA is generally oxidized to the correspondingly substituted quinacridone according to the present process.

The quinacridone compounds produced according to the present process are useful as pigments. Of particular significance as pigments are the unsubstituted (wherein X and Y are H) and 4,11- and 2,9-disubstituted quinacridones, especially 4,11- and 2,9-dichloroquinacridone, 4,11- and 2,9-dimethylquinacridone, and 2,9-difluoroquinacridone.

The present process is also useful for producing solid solutions which contain a quinacridone component. In order to produce a solid solution of quinacridone compounds, the paste contains two or more DQA compounds which correspond to QA compounds that form a solid solution. Usually such solid solutions are binary or ternary solid solutions containing two or three quinacridone compounds. Solid solutions containing two or more quinacridone compounds are well-known in the art. It is also possible to prepare mixed solid solutions which comprise one or more quinacridone compounds and a compound from a different chemical class, for example, a diaryldiketopyrrolopyrrole. To form such solid solutions, the paste contains the compound from a different class and the DQA. Such solid solutions are also known in the art.

Oxidizing agents that are suitable for oxidizing a DQA to a QA are well-known to the skilled artisan. Any such oxidizing agent is suitable for use in the present process. For example, aromatic compounds that contain a nitro group, such as nitrobenzenes, nitrophenols, nitrotoluenes and nitrobenzenesulfonic and carboxylic acids, in particular nitrobenzene, m-nitrobenzenesulfonic acid and salts thereof, p-nitrotoluene, m-nitrophenol, pnitrobenzoic acid, m-nitrobenzoic acid, 4nitrophthalic acid, and 2-methyl-5-nitrobenzenesulfonic acid and salts thereof, are suitable for use in the present process. However, the use of a quinone compound and molecular oxygen as the oxidizing agent is preferred.

The use of a quinone compound and molecular oxygen as an oxidizing agent to convert DQA compounds to QA compounds is well-known in the art As discussed above, the quinone compound has been described in the literature both as a catalyst and as an oxidizing agent It is believed that the quinone is an oxidizing agent which is reduced to the corresponding leuco compound during the oxidation of the DQA. The molecular oxygen regenerates the quinone so that less than the stoichiometric amount of the quinone is required for the reaction to proceed to completion. Under the present reaction conditions, a much smaller molar amount of the quinone compound is required than in oxidations carried out by bubbling molecular oxygen through a reaction mixture which is a solution or suspension comprising the DQA to be oxidized. Thus, it is preferred to utilize a quinone compound which is regenerated by molecular oxygen and which is present in less than the stoichiometric amount, as oxidizing agent.

Suitable quinone compounds are, for example, anthraquinones, phenanthraquinones or napthaquinones, especially their sulfonic acid and carboxylic acid derivatives, or salts thereof. Anthraquinone and its derivatives such as mono- or di-chloroanthraquinone or the anthraquinone mono- or di-sulfonic acids, especially anthraquinone-2-sulfonic acid or anthraquinone-2,6-disulfonic acid and their derivatives, such as their salts, are particularly suitable. Generally, the quinone compound is an anthraquinone mono- or di-sulfonic acid, or a salt thereof. Anthraquinone-2-sulfonic acid and its salts are preferred quinone compounds. The acid salts are preferably alkali metal salts.

The quinone compound is present in an amount which is effective to oxidize the DQA compound to the corresponding QA compound. It is preferred, in the interest of operating economy to use less than the stoichiometric amount of the quinone compound and to regenerate it in situ by exposing the resulting leuco compound to an oxidizing agent, such as molecular oxygen, for example by exposure to air. In general, the quinone compound is present an amount ranging from 0.005 to 0.15 times, preferably 0.01 to 0.09 times, especially 0.01 to 0.02 times, the weight of the DQA.

In general, the reaction proceeds if the high shear force mixing is carried out under an atmosphere of at least 2 percent by volume of molecular oxygen, the rest being a gas which is inert under the reaction conditions, for example, oxygen/nitrogen or oxygen/argon mixtures. In a specific embodiment of this invention, the oxygen-containing gas is air. If no volatile organic compounds are present in the paste, the mixing step is preferably carried out in a system that is open to the atmosphere, for example under ambient air in a vessel open to the atmosphere. The ability to operate the present process in a system that is open to the atmosphere is an additional advantage of the present process.

Since the DQA and oxidizing agent are normally solids, it is usually necessary to add a liquid to these solids to form a paste. In general, any effective paste forming amount of a liquid which does not adversely effect the reaction is suitable.

In general, the high shear force mixing, in the absence of additional heating, inputs sufficient energy for the oxidation reaction to proceed at a reasonable rate. However, it is possible to also provide additional control of the reaction rate by controlling the reaction temperature. Preferably, the oxidation is carried out at a temperature of from 60° to 90° C.

It is necessary for the paste to also comprise a base for the oxidation to proceed at a reasonable rate. The base functions to facilitate the oxidation reaction by forming a salt of the DQA. Generally, it is preferred to use a strong base. Suitable bases include the alkali metal hydroxides, for example sodium and potassium hydroxide, and quaternary ammonium hydroxides. The base is preferably present in relatively small amounts compared to known oxidation reactions wherein DQA is oxidized to QA. The requirement to utilize only a small amount of base, if any, is an additional advantage of the present process over known processes. Preferably, the base is present in an amount which is from 0.5 to 1 mole per mole of DQA. Most preferably the base is present in an amount which is from 0.6 to 0.80 moles per mole of DQA. Generally, the paste contains from 0.01 to 0.4 parts of base per part of the DQA, depending on the identity of the base. Most preferably, the base is sodium or potassium hydroxide and is present in an amount of from 0.05 to 0.1 parts per part of the DQA.

Although the reaction proceeds reasonably well if water is the paste forming liquid, it is advantageous for the paste to comprise a small amount of an organic conditioning agent. The organic conditioning agent is a volatile organic liquid or a non-volatile organic liquid, or a mixture thereof. Preferably, the organic conditioning agent is a non-volatile organic liquid, or a mixture of non-volatile organic liquids.

Most preferably, the organic conditioning agent is both non-volatile and miscible with or soluble in water. Utilizing a water soluble organic conditioning agent facilitates the separation of the pigment product from the auxiliaries. It is advantageous to use a non-volatile organic liquid so that the reaction vessel can be open to the atmosphere without risk of environmental damage or explosion.

Suitable non-volatile organic liquids include glycols, such as triethylene glycol and dipropylene glycol, and polyglycols. Especially useful organic conditioning agents include polyethylene glycols having a molecular weight in the range from 200 to 600. Most preferably, the liquid is a polyethyleneglycol with a molecular weight of about 400.

The organic conditioning agent, if present, contributes to the physical characteristics of the paste. It is possible for the organic conditioning agent to be the only liquid utilized to form the paste. However, it is preferred to utilize the organic conditioning agent in conjunction with some water to form the paste.

In addition to forming a paste, it appears that the organic conditioning agent also functions to facilitate the oxidation reaction in some unknown manner. However, a very small amount of organic conditioning agent is sufficient to facilitate the oxidation reaction.

It is preferred for the paste to contain from 0.01 to 0.2 parts of the organic conditioning agent per part of paste. Most preferably, the paste contains from 0.05 to 0.15 parts of the organic conditioning agent per part of paste.

The paste advantageously also comprises a grinding aid. In general, the grinding aid is a known grinding aid for pigment conditioning. For example, sodium chloride, sodium sulfate and calcium chloride are all suitable for the present process and known as grinding aids in pigment milling processes. The presence of a grinding aid permits the oxidation of the DQA and conditioning of the QA product to proceed simultaneously to yield a pigmentary product directly from the present process; rather than producing a pigment crude which would require a further particle-size-reducing aftertreatment in order to be of pigmentary quality. Pigmentary quality product denotes a product that is useful in pigment applications without further particle-size-reducing aftertreatinents.

Preferably, the grinding aid is water-soluble in order to facilitate separation from the QA product.

The paste commonly contains a small amount of water and can contain a considerable amount of water. Generally, the water is present at least due to the hygroscopic nature of the base and/or grinding aid. In addition, water is produced by the oxidation reaction. The base is also conveniently added to the mixture as a commercially available, concentrated solution in water. In general, the amount of water present in the concentrated solution is inconsequential to the progress of the oxidation. However, too much water can adversely effect the reaction by diluting the base or other reactants. In addition, the amount of water present effects the crystal phase of the product in the case of unsubstituted quinacridones.

In an embodiment, the paste comprises the DQA, an effective paste-forming amount of an water and/or an organic conditioning agent, an effective reaction-facilitating amount of base and an effective oxidizing amount of an oxidizing agent, preferably wherein the oxidizing agent is a quinone compound which is regenerated by molecular oxygen and the mixing step is carried out under an air atmosphere.

In an alternate embodiment, the paste comprises the DQA, from 1 to 6 parts by weight of a grinding aid per part of DQA, an effective paste forming amount of water and/or an organic conditioning agent, an effective reaction-facilitating amount of base and an effective oxidizing amount an oxidizing agent, preferably wherein the oxidizing agent is a quinone compound which is regenerated by molecular oxygen and the mixing step is carried out under an air atmosphere.

Preferably, the paste comprises 1 part of DQA, from 2 to 4 parts by weight of a grinding aid, water, from 0.1 to 0.8 parts by weight of an organic conditioning agent, from 0.05 to 0.4 parts by weight of a base and an effective oxidizing amount of an oxidizing agent, wherein the combined amounts of the water and the organic conditioning agent are effective to form a paste. Preferably, the oxidizing agent is a quinone compound which is regenerated by molecular oxygen and the mixing step is carried out under an air atmosphere. Most preferably, the quinacridone product is in pigmentary form and the organic conditioning agent is polyethylene glycol having a molecular weight of about 400.

After the high shear force mixing step, the resulting QA pigment is isolated by methods known in the art In particular, the product is added to hot water and optionally neutralized or acidified and isolated by conventional filtration techniques.

If a particular crystal form of the resulting QA is desired, the crystal phase is controlled by seeding the paste with a small amount of the desired crystal phase. For example, if the DQA is unsubstituted, the presence of a small amount of gamma-phase QA in the paste yields gamma-phase QA as the product.

Although the paste can consist essentially of or consist of the DQA, water and/or organic conditioning agent, the base, the oxidizing agent and optionally the grinding aid, pastes which contain additional components, such a crystal-phase-directing seed or a solid-solution-forming compound, are within the scope of the invention.

The following examples further describe but do not limit the scope of the present invention. All parts given are parts by weight unless otherwise specified.

Equipment:

All kneading is carried out in a heavy duty, laboratory kneader-mixer, 0.5 liter volume (0.3 liter working capacity) with two sigma blades rotating at 36 and 62 RPM, respectively.

EXAMPLE 1

100 g salt (Morton TFC-325)(sodium chloride) and 25 g alpha phase dihydroquinacridone (DQA) are added to a kneader. The mixture is briefly dry blended and then mixed with 20 g polyethylene glycol, m.w. 400 (PEG 400). Then 4 g of 50% NaOH and 2.6 g water are added. Finally, 0.6 g of anthraquinone sulfonate, Na salt (AQS), 76% solids aqueous presscake, is added. The resulting paste is heated by water flowing through the jacketed kneading chamber at about 60° C. While mixing in the kneader, the viscous paste gradually becomes darker in color with the internal temperature of the vessel rising to about 70° C. Three hours after the AQS addition, the run is terminated and the contents removed. The mass is broken into small pieces and added to 500 ml of warm water. The slurry is finally homogenized in a blender and then filtered, washed and dried. XRD analysis shows the bright red product to be alpha phase quinacridone (QA); (analysis: QA, 93.2%, quinacridonequinone (QAQ), 0.8%, DQA, 0.1%).

EXAMPLE 2

Example one is repeated except that 0.5 g gamma quinacridone is added to the dry mix. XRD shows the red product to be gamma phase quinacridone; (analysis: QA, 93.8%, QAQ, 0.9%, DQA, 1.4%).

EXAMPLE 3

Example one is repeated except that the 2.6 g additional water is omitted XRD shows the red product to be gamma phase quinacridone; (analysis: QA, 94.8%, QAQ, 0.4%, DQA, 0.4%).

EXAMPLE 4

80 g salt, 40 g DQA and 0.8 g beta quinacridone crude are added to a kneader. The mixture is briefly dry blended and then 16 g PEG 400 is added with mixing. Then 5.6 g of 50% NaOH and 3.7 g of water are added. Finally, 1.0 g of AQS, 76% solids aqueous presscake is added. The resulting paste is heated by water flowing through the jacketed kneading chamber at about 60° C. While mixing, the viscous paste gradually becomes darker in color with internal temperature rising to about 78°. Three hours after AQS addition, the run is terminated, and the contents removed. The mass is broken into small pieces and added to 500 ml of warm water in a one liter flask. The slurry is heated with stirring for one half hour at 80° and then filtered, washed and dried. XRD analysis shows the violet product to be beta phase quinacridone; (analysis: QA, 93.8%, QAQ, 1.5%, DQA, 1.2%).

EXAMPLE 5

124 g salt and 31 g 2,9-dimethyldihydroquinacridone (Me$_2$DQA) are added to a kneader. The mixture is briefly dry blended and then 20 g PEG 400 is added with mixing. Then 5.7 g of 45% KOH and 0.9 g water are added. Finally, 0.6 g of AQS, 76% solids aqueous presscake, is added. The resulting paste is heated by water flowing through the jacketed kneading chamber at about 60° C. While mixing, the viscous paste gradually becomes darker in color with internal temperature rising to about 71°. Three hours after AQS addition, the run is terminated, and the contents removed. The mass is broken into small pieces and added to 500 ml of warm water in a one liter flask. The slurry is heated with stirring for one half hour at 80° and then filtered, washed and dried XRD analysis shows the magenta product to be a mixture of alpha and beta phase 2,9-dimethylquinacridone; (analysis: Me$_2$QA, 93.8%, Me$_2$QAQ, 1.7%, Me$_2$DQA, 3.1%).

EXAMPLE 6

105 g salt and 35 g 2,9-dichlorodihydroquinacridone (Cl$_2$DQA) are added to a kneader. The mixture is briefly dry blended. 16 g of PEG 400 is then added with mixing. Then 5.0 g of 50% NaOH and 2.0 g water are added. Finally, 0.9 g of AQS, 76% solids aqueous presscake, is added. The resulting paste is heated by water flowing through the jacketed kneading chamber at about 60° C. While mixing, the viscous paste gradually becomes darker in color with internal temperature rising to about 73°. Viscosity is lowered by an additional 2 g water. One hour after AQS addition a sample is taken and extracted with hot water and dried. Analysis shows: Cl$_2$QA, 69.8%, Cl$_2$QAQ, 1.6%, Cl$_2$DQA, 25.4%). A second sample at two hours and similarly extracted shows Cl$_2$QA, 91.9%, Cl$_2$QAQ, 2.6%, Cl$_2$DQA, 1.6%). The run is terminated after three hours and the contents removed. The mass is broken into small pieces and added to 500 ml of warm water in a one liter flask. The slurry is heated with stirring for one half hour at 80° and then filtered, washed and dried. XRD analysis shows the magenta product to be a pure gamma-phase 2,9Aichloroquinacridone.

Hoover Muller rubout of the product vs. a commercial Cl$_2$QA magenta shows a characteristically blue masstone and yellow, intense tint color.

EXAMPLE 7

112 g salt, 16.8 g DQA and 11 g 2,9-dichlorodihydroquinacridone are added to a kneader. The mixture is briefly dry blended. 20 g PEG 400 is added with mixing. Then 4 g of 50% NaOH and 2.6 g water are added. Finally, 0.6 g of AQS, 76% solids aqueous presscake, is added. The resulting paste is heated by water flowing through the jacketed kneading chamber at about 60° C. While mixing, the viscous paste gradually becomes darker in color with internal temperature rising to about 71°. Three hours after AQS addition the run is terminated and the contents removed. The mass is broken into small pieces and added to 500 ml of warm water in a one liter flask. The slurry is heated with stirring for one half hour at 80° and then filtered, washed and dried. XRD analysis shows the red product to be the characteristic solid solution (60/40) of quinacridone and 2,9-dichloroquinacridone. Analysis shows: QA, 61.6%, Cl$_2$QA, 38.4%.

EXAMPLE 8

120 g salt (Morton TFC-325), 30 g DQA are added to a kneader. The mixture is briefly dry blended and then 15 g PEG 400 and 4.8 g of 50% NaOH are added with mixing. An additional 6.3 g PEG 400 is added along with 0.7 g AQS. The resulting paste is heated by water flowing through the jacketed kneading chamber at about 60° C. While mixing, the viscous paste gradually becomes purple in color with internal temperature rising to about 73°. Two hours after AQS addition, 0.5 g of phthalimldomethylquinacridone is added and mixing continued for an additional two hours. The run is terminated and the contents removed from the kneader. The mass is broken into small pieces and added to 500 ml of warm water in a one liter flask. The slurry is heated with stirring for one half hour at 80° and then filtered, washed and dried.

Hoover muller rubout of the product shows a characteristically dark masstone color comparable to a commercial red beta quinacridone pigment with a strong intense tint color.

EXAMPLE 9

100 g salt and 25 g DQA are added to a kneader. The mixture is briefly dry blended and then mixed with 28 g dipropylene glycol. Then 4 g of 50% NaOH and 2.6 g water are added. While mixing in the kneader an additional 4 g of dipropylene glycol is added. The resulting paste is heated by water flowing through the jacketed kneading chamber at about 60° C. Finally, 0.6 g of anthraquinone sulfonate, Na salt (AQS), 76% solids aqueous presscake, is added. The viscous paste gradually becomes darker in color with the internal temperature of the vessel rising to about 69°. Three hours after the AQS addition, the run is terminated and the contents removed. The mass is broken into small pieces and added to 500 ml of warm water. The slurry is finally homogenized in a blender and then filtered, washed and dried. XRD analysis shows the bright red product to be alpha phase QA; (analysis: QA, 64.1%, QAQ, 0.4%, DQA, 35.6%).

EXAMPLE 10

100 g salt and 25 g DQA are added to a kneader. The mixture is briefly dry blended and then mixed with 20 g triethylene glycol. Then $^4$ g of 50% NaOH and 2.6 g water are added. While mixing in the kneader an additional 4 g of triethylene glycol is added. The resulting paste is heated by water flowing through the jacketed kneading chamber at about 60° C. Finally, 0.6 g of anthraquinone sulfonate, Na salt (AQS), 76% solids aqueous presscake, is added. The viscous paste gradually becomes darker in color with the internal temperature of the vessel rising to about 70°. Three hours after the AQS addition, the run is terminated and the contents removed. The mass is broken into small pieces and added to 500 ml of warm water. The resulting slurry is heated to 80° and stirred for about one half hour and then filtered, washed and dried. XRD analysis shows the bright red product to be alpha phase QA; (analysis: QA, 69.1%, QAQ, 0.4%, DQA, 29.9%).

EXAMPLE 11

100 g salt and 25 g alpha phase DQA are added to a kneader. The mixture is briefly dry blended and then mixed with 20 g PEG 400. Then 4 g of 50% NaOH and 2.0 g water are added. The resulting paste is heated by water flowing through the jacketed kneading chamber at about 60° C. Finally, 14 g of m-nitrobenzenesulfonic acid, sodium salt, are added in 2 g increments every 15 minutes while mixing in the kneader. The viscous paste gradually becomes darker in color with each addition. The internal temperature of the vessel rises to about 78°. After a total of 2 hours of mixing, the is terminated and the contents removed The mass is broken into small pieces and added to 500 ml of warm water. The resulting slurry is heated to 80° and stirred for about one half hour and then filtered, washed and dried. XRD analysis shows the bright red product to be a mixture of alpha and beta phase quinacridone (analysis QA 92.8%, QAQ 5.3%, DQA 0.1%).

EXAMPLE 12

80 g salt and 40 g DQA are added to a kneader. The mixture is briefly dry blended and then mixed with 28 g dipropylene glycol. Then 28 g of 50% NaOH and 18 g water are added The resulting paste is heated by water flowing through the jacketed kneading chamber at about 60° C. Finally, 1.0 g of anthraquinone sulfonate, Na salt (AQS), 76% solids aqueous presscake, is added. The viscous paste gradually becomes darker in color with the internal temperature of the vessel rising to about 75°. After two hours the process yields a product which contains 36% of alpha phase QA.

EXAMPLE 13

100 g salt and 25 g DQA are added to a kneader. The mixture is briefly dry blended and then mixed with 5 g PEG-400. Then 16 g of 50% NaOH and 25.6 g water are added. The resulting paste is heated by water flowing through the jacketed kneading chamber at about 60° C. Finally, 0.6 g of anthraquinone sulfonate, Na salt (AQS), 76% solids aqueous presscake, is added. The viscous paste gradually becomes darker in color with the internal temperature of the vessel rising to about 70°. After two hours the process yields a product which contains 88.6% of alpha phase QA.

EXAMPLE 14

80 g salt and 40 g DQA are added to a kneader. The mixture is briefly dry blended and then mixed with 10 g PEG-400. Then 28 g of 50% NaOH and 18 g water are added. The resulting paste is heated by water flowing through the jacketed kneading chamber at about 60° C. Finally, 1.0 g of anthraquinone sulfonate, Na salt (AQS), 76% solids aqueous presscake, is added The viscous paste gradually becomes darker in color with the internal temperature of the vessel rising to about 70°. After 4 hours the process yields a product which contains 90.9% of alpha phase QA.

I claim:

1. A process for preparing an unsubstituted or substituted quinacridone from a correspondingly substituted dihydroquinacridone, which process comprises subjecting a paste containing the dihydroquinacridone and an effective oxidizing amount of an oxidizing agent which is an aromatic compound containing a nitro group or a quinone compound plus molecular oxygen, in the presence of an effective reaction-facilitating amount of a strong base, to a high shear force mixing step.

2. A process of claim 1, wherein the paste comprises 0.5 to 1 mole of the base.

3. A process of claim 1 wherein the paste comprises an effective paste-forming amount of water and/or an organic conditioning agent.

4. A process of claim 1 wherein the paste comprises a grinding aid.

5. A process of claim 1 wherein the quinacridone is unsubstituted quinacridone or a 4,11- or 2,9-disubstituted quinacridone.

6. A process of claim 5 wherein the quinacridone is selected from the group consisting of unsubstituted quinacridone, 4,11-dichloroquinacridone, 2,9-dichloroquinacridone, 4,11-dimethylquinacridone, 2,9-dimethylquinacridone and 2,9-difluoro quinacridone.

7. A process of claim 1 wherein the quinacridone is a component of a solid solution.

8. A process of claim 1 wherein the oxidizing agent is a quinone compound which is regenerated by molecular oxygen and which is present in less than the stoichiometric amount.

9. A process of claim 1 wherein the base is an alkali metal hydroxide or a quaternary metal hydroxide.

10. A process of claim 9 wherein the paste comprises 0.6 to 0.8 moles of base per mole of dihydroquinacridone.

11. A process of claim 3 wherein the organic conditioning agent is an organic liquid which is substantially non-volatile under the mixing conditions.

12. A process of claim 11 wherein the organic conditioning agent is polyethylene glycol having a molecular weight of about 400.

13. A process of claim 1 wherein the paste comprises an effective paste-forming amount of a mixture of water and an organic liquid which is substantially non-volatile under the mixing conditions.

14. A process of claim 13 wherein the organic conditioning agent is polyethylene glycol having a molecular weight of about 400.

15. A process of claim 13 wherein the paste comprises from 0.01 to 0.2 parts of the organic conditioning agent per part of paste.

16. A process of claim 4 wherein the quinacridone is in pigmentary form.

17. A process of claim 1 wherein the paste comprises the dihydroquinacridone an effective paste-forming amount of water and/or an organic conditioning agent, an effective reaction-facilitating amount of sodium or potassium hydroxide as base and an effective oxidizing amount of the oxidizing agent.

18. A process of claim 1 wherein the paste comprises 1 part of dihydroquinacridone from 2 to 4 parts by weight of a grinding aid, water, from 0.1 to 0.8 parts by weight of an organic conditioning agent, from 0.05 to 0.2 parts by weight of a base and an effective oxidizing amount of an oxidizing agent, wherein the combined amounts of the water and the organic conditioning agent are effective to form the paste.

19. A process of claim 18 wherein the quinacridone is in pigmentary form.

20. A process of claim 19 wherein the organic conditioning agent is polyethylene glycol having a molecular weight of about 400.

21. A process of claim 1 wherein the aromatic compound containing a nitro group is selected from the group consisting of nitrobenzene, m-nitrobenzenesulfonic acid and salts thereof, p-nitrotoluene, m-nitrophenol, p-nitrobenzoic acid, m-nitrobenzoic acid, 4-nitrophthalic acid and 2-methyl-5-nitrobenzenesulfonic acid and salts thereof.

* * * * *